US006537970B1

(12) United States Patent
Vulpescu et al.

(10) Patent No.: US 6,537,970 B1
(45) Date of Patent: *Mar. 25, 2003

(54) PHARMACEUTICAL COMPOSITION

(75) Inventors: Dan-Gabriel Vulpescu, Bremerhaven (DE); Brigitte Freudensprung, Holzkirchen (DE)

(73) Assignee: Hexal AG, Holzkirchen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/486,348

(22) PCT Filed: Aug. 27, 1998

(86) PCT No.: PCT/EP98/05454

§ 371 (c)(1), (2), (4) Date: Feb. 25, 2000

(87) PCT Pub. No.: WO99/09964

PCT Pub. Date: Mar. 4, 1999

(30) Foreign Application Priority Data

Aug. 27, 1997 (DE) .......................................... 197 37 348

(51) Int. Cl.⁷ ........................ A61K 31/70; A61K 31/425
(52) U.S. Cl. ......................................... 514/25; 514/396
(58) Field of Search .................................. 514/25, 396

(56) References Cited

U.S. PATENT DOCUMENTS

| 4,318,853 A | 3/1982 | Ayer et al. |
| 5,160,737 A | 11/1992 | Friedman et al. |

OTHER PUBLICATIONS

"Recurrent Bacterial Vaginosis", Hay, Philip E., *Dermatologic Clinics*, vol. 16, No. 4, Oct. 1998: pp. 769–773.

"Vaginal Infections In Adult Women", Sobel, J.D., *The Medical Clinics of North America*, vol. 74, No. 6, Nov. 1990: pp. 1573–1602.

*Rote Liste 1997*, No. 46 071 and No. 46 098.

*Primary Examiner*—Zohreh Fay
(74) *Attorney, Agent, or Firm*—Cohen, Pontani, Lieberman & Pavane

(57) ABSTRACT

The invention relates to a novel pharmaceutical combination comprising clindamycin and clotrimazole for use for vaginal infections.

12 Claims, No Drawings

PHARMACEUTICAL COMPOSITION

BACKGROUND OF THE INVENTION

This is a National Stage Application based on PCT/EP98/05454 filed Aug. 27, 1998 designating the United States of America.

The present invention is in a novel pharmaceutical composition comprising a combination of clindamycin and clotrimazole for vaginal use for bacterial infections, fungal infections or mixed infections of the vagina.

Conventional therapies for the treatment of bacterial infections of the vagina, such as, for example, bacterial vaginosis, which are caused by the interaction of Gardnerella vaginalis and anaerobic bacteria, feature treatments with chemotherapeutics acting on anaerobes and protozoa, such as, for example, metronidazole or tinidazole, or the treatment with an antibiotic, such as amoxicillin or clindamycin. Treatment is carried out either orally or by topical vaginal application.

The oral therapy with one of these active compounds has considerable disadvantages, such as the occurrence of considerable adverse effects or else undesirable interactions with other medicaments. Moreover, metronidazole is suspected of having a carcinogenic potential. In any case, the topical therapy is preferred to a systemic therapy to avoid systemic burden on the body.

Hitherto, topical therapies with metronidazole had dosages of from 500 to 1000 mg of metronidazole as a single dose or, in the case of a 5-day-therapy, 200–500 mg of metronidazole per day. If the active compound is administered in a semi-solid preparation, for example as a gel or cream, doses of about 100 mg per day are customary. Analogous amounts are employed in the case of the active compound clindamycin. However, even in a topical therapy, the same or similar side effects have been described as in the oral use of the active compounds.

A considerable disadvantage of the above-described therapies with an antibiotic or a chemotherapeutic is the fact that, in the case of both oral and topical therapy, a secondary infection, such as vaginal candidosis frequently occurs, or a mixed infection, within the month following the treatment, thus requiring another treatment with a further medicament. In this case, a very accurate and complicated diagnosis is required to determine which kind of colpitis is present, so that the right drugs for the treatment can be selected.

One of the most frequent consequent infections is vaginal candidosis, a fungal infection requiring treatment with an antimycotic, such as clotrimazole.

Clotrimazole is a local antimycotic with a broad activity spectrum comprising many fungi which are pathogenic to humans. In gynecology, clotrimazole is mainly used as monotherapy for the treatment of vulvovaginal infections by yeasts or Blastomycetes. In topical therapy with clotrimazole, dosages of 500 mg are used in the case of a single application. Dosages of about 100–200 mg of clotrimazole are employed in treatment therapies lasting for several days. Furthermore, it is known that clotrimazole, in addition to the antimycotic action, has a slight antibacterial action.

It is the object of the invention to provide a pharmaceutical composition for the treatment of vaginal disorders, which reduces side effects and makes the treatment more simple and more efficient.

THE INVENTION

The object of the invention is achieved by a novel pharmaceutical composition which comprises, as active components, clindamycin and clotrimazole in combination.

Surprisingly, it has been found that lower dosages are required when administered in combination than in the case of the treatment with the individual active compounds. The combination shows a considerable synergistic effect. Whereas according to the prior art, clindamycin has to be administered in topical therapy in doses of 100–200 mg per day to effect a complete cure of the disorder, in the case of the novel combination, the clindamycin dose can be reduced to 10–80 mg, preferably to 20–50 mg. Depending on the severity of the disorder, doses of 10–80 mg, preferably of 20–50 mg, of clindamycin are administered in combination with 50–150 mg, preferably 50–100 mg, of clotrimazole.

The novel pharmaceutical composition is preferably intended for local use in the treatment of vaginal infections.

In addition to the active components, the pharmaceutical composition optionally includes pharmaceutically acceptable carriers or auxiliaries. Preferred administration forms are vaginal suppositories, vaginal tablets, vaginal ovula, vaginal rings or semi-solid vaginal preparations such as ointments, creams or gels.

Customary tablet auxiliaries include:

starch, for example corn starch, rice starch, potato starch, wheat starch, milk sugar (lactose), glucose, sucrose, micro-crystalline cellulose, colloidal silica, magnesium stearate, stearic acid, talc, polyvinylpyrrolidone (linear and cross-linked), sodium chloride, polyethylene glycol, hydroxypropyl-methylcellulose, hydroxypropylcellulose, gelatin, calcium phosphate, cellulose, mannitol, sodium carboxymethylstarch, sodium carbonate, sodium bicarbonate, calcium carbonate, sodium carboxymethylcellulose (linear and crosslinked) and magnesium stearate.

For further tablet auxiliaries, see "Die Tablette, Grundlagen und Praxis des Tablettierens, Granulierens und Dragierens" [The Tablet, Basics and Practice of Tableting, Granulating and Coating] by W. A. Ritschel, pp. 85–144, and "Katalog pharmazeutischer Hilfsstoffe" [Catalog of Pharmaceutical Auxiliaries] edited by a team from Ciba-Geigy, Hoffmann-La Roche and Sandoz, Basle 1974.

Customary auxiliaries for creams include:

sorbitan monostearate, Polysorbate 60, cetyl palmitate, paraffin, cetylstearyl alcohol, benzyl alcohol, silica, triacetin, isopropyl monostearate, polyethylene glycol, glycerol monostearate, polyacrylic acid, sodium hydroxide, docusate sodium, dimethicone, triglycerides, octyldecanol and octyldodecanol.

Customary auxiliaries for ovula include:

gelatin, glycerol, polyethylene glycol, hydrogenated fat, cetostearyl alcohol polyethylene glycol ether, sodium dodecyl sulfate, glycerol (mono-, di-, tri-)fatty acid ester (C12–C18)polyethylene glycol dodecyl ether mixture, paraffin, ethyl 4-hydroxybenzoate, propyl 4-hydroxybenzoate and petroleum jelly.

The vaginal tablets can be in the form of monolayer, two-layer or three-layer tablets or as tablets with an effervescent composition.

The active components of the novel composition are present in concentrations of 10–80 mg of clindamycin and 50–150 mg of clotrimazole, preferably 20–50 mg of clindamycin and 50–100 mg of clotrimazole, in particular 20 mg of clindamycin and 100 mg of clotrimazole, per use or dose unit.

The novel combination can be employed for treating a large number of vaginal disorders. Thus, it is possible to treat successfully the most frequent colpitides, Candida colpitis (fungal infection) and bacterial vaginosis (bacterial mixed infection).

Furthermore, the combination according to the invention permits the treatment of so-called mixed infections caused by bacteria and fungi. When applying the combination according to the invention, both pathogens are controlled simultaneously.

Indistinct infections usually require extremely complicated diagnostic determinations. When treating such disorders with the combination of clindamycin and clotrimazole, this is considerably reduced, since it is virtually immaterial which type of colpitis is present.

In the monotherapy of an infection with an antibiotic of the prior art, the most frequent secondary infection is a candidosis. When the combination according to the invention is used in the treatment, such secondary infections can be prevented. Thus, on the one hand further treatment, which is very unpleasant for the patient and associated with a prolonged duration of treatment, is no longer required and, on the other hand, from the point of view of health policy, the financial costs can be reduced considerably by the combination therapy.

The invention is illustrated in more detail by the examples below, but without thus limiting the scope of the invention.

EXAMPLE 1

| Monolayer tablet | |
| --- | --- |
| Clotrimazole | 100.0 mg |
| Clindamycin-HCl (corresponds to 20 mg of clindamycin) | 22.7 mg |
| Lactose D20 | 265.0 mg |
| Corn starch | 33.3 mg |
| Hydroxypropylcellulose (HPC) (Klucel EF) | 2.0 mg |
| Calcium lactate · 5 $H_2O$ | 30.0 mg |
| Lactic acid | 41.0 mg |
| Microcrystalline cellulose (Avicel PH 102) | 128.0 mg |
| Kollidon CL | 12.0 mg |
| Aerosil 200 | 7.0 mg |
| Magnesium stearate | 7.0 mg |

Clotrimazole, clindamycin-HCl, lactose, some of the corn starch, HPC, calcium lactate and lactic acid are granulated in a fluidized-bed granulator. The resulting granules and the remainder of the corn starch, Kollidon, microcrystalline cellulose, magnesium stearate and Aerosil are passed through a forced sieve (1.25 mm) and homogenized in a container mixture. The resulting mixture is tableted on a rotating tableting machine.

EXAMPLE 2

| Monolayer tablet | |
| --- | --- |
| Clotrimazole | 100.0 mg |
| Clindamycin-HCl (corresponds to 20 mg of clindamycin) | 22.7 mg |
| Lactose D20 | 265.0 mg |
| Corn starch | 33.3 mg |
| HPC (Klucel EF) | 2.0 mg |
| Calcium lactate · 5 $H_2O$ | 90.0 mg |
| Lactic acid | 35.0 mg |
| Microcrystalline cellulose (Avicel PH 102) | 128.0 mg |
| Kollidon CL | 12.0 mg |
| Aerosil 200 | 7.0 mg |
| Magnesium stearate | 7.0 mg |

Using the components stated above, a tablet is prepared analogously to Example 1.

EXAMPLE 3

| Monolayer tablet | |
| --- | --- |
| Clotrimazole | 100.0 mg |
| Clindamycin-HCl (corresponds to 20 mg of clindamycin) | 22.7 mg |
| Lactose D20 | 795.3 mg |
| Corn starch | 100.0 mg |
| HPC (Klucel EF) | 5.0 mg |
| Calcium lactate · 5 $H_2O$ | 30.0 mg |
| Lactic acid | 70.0 mg |
| Microcrystalline cellulose (Avicel PH 102) | 384.5 mg |
| Kollidon CL | 35.0 mg |
| Aerosil 200 | 23.0 mg |
| Magnesium stearate | 22.5 mg |

Clotrimazole, clindamycin-HCl, lactose, some of the corn starch, some of the microcrystalline cellulose, HPC, calcium lactate and lactic acid are granulated in a fluidized-bed granulator. The resulting granules and the remainder of the corn starch and the microcrystalline cellulose, Kollidon, magnesium stearate and Aerosil are passed through a forced sieve (1.25 mm) and homogenized in a container mixture. The resulting mixture is tableted on a rotating tableting machine.

EXAMPLE 4

| Two-layer tablet | | |
| --- | --- | --- |
| | 1st layer | 2nd layer |
| Clotrimazole | 100.0 mg | — |
| Clindamycin-HCl (corresponds to 20 mg of clindamycin) | — | 22.7 mg |
| Lactose D20 | 265.0 mg | 265.0 mg |
| Corn starch | 33.0 mg | 33.6 mg |
| HPC (Klucel EF) | 2.0 mg | 2.0 mg |
| Calcium lactate · 5 $H_2O$ | 90.0 mg | 10.0 mg |
| Lactic acid | 35.0 mg | 23.0 mg |
| Microcrystalline cellulose (Avicel PH 102) | 128.0 mg | 128.0 mg |
| Kollidon CL | 12.0 mg | 12.0 mg |
| Aerosil 200 | 7.0 mg | 7.7 mg |
| Magnesium stearate | 7.0 mg | 7.0 mg |

Using the components mentioned above, on the one hand granules for the first layer and on the other granules for the second layer are prepared analogously to Example 1, and the granules are tableted to give a two-layer tablet.

EXAMPLE 5

| Two-layer tablet | | |
| --- | --- | --- |
| | 1st layer | 2nd layer |
| Clotrimazole | 100.0 mg | — |
| Clindamycin-HCl (corresponds to 20 mg of clindamycin) | — | 22.7 mg |
| Lactose D20 | 265.0 mg | 265.0 mg |
| Corn starch | 33.0 mg | 33.6 mg |
| HPC (Klucel EF) | 2.0 mg | 2.0 mg |
| Calcium lactate · 5 $H_2O$ | 90.0 mg | — |
| Lactic acid | 35.0 mg | — |
| Microcrystalline cellulose (Avicel PH 102) | 128.0 mg | 128.0 mg |
| Kollidon CL | 12.0 mg | 12.0 mg |

-continued

Two-layer tablet

|  | 1st layer | 2nd layer |
|---|---|---|
| Aerosil 200 | 7.0 mg | 7.7 mg |
| Magnesium stearate | 7.0 mg | 7.0 mg |

Using the components mentioned above, a tablet is prepared analogously to Example 4.

EXAMPLE 6

Monolayer tablet

| Clotrimazole | 100.0 mg |
|---|---|
| Clindamycin-HCl (corresponds to 10 mg of clindamycin) | 11.4 mg |
| Lactose D20 | 265.0 mg |
| Corn starch | 33.6 mg |
| HPC (Klucel EF) | 2.0 mg |
| Calcium lactate · 5 H$_2$O | 90.0 mg |
| Lactic acid | 35.0 mg |
| Microcrystalline cellulose (Avicel PH 102) | 128.0 mg |
| Kollidon CL | 12.0 mg |
| Aerosil 200 | 7.0 mg |

Using the components mentioned above, a tablet is prepared analogously to Example 1.

EXAMPLE 7

Two-layer tablet

|  | 1st layer | 2nd layer |
|---|---|---|
| Clotrimazole | 150.0 mg | — |
| Clindamycin-HCl (corresponds to 30 mg of clindamycin) | — | 34.1 mg |
| Lactose D20 | 280.0 mg | 280.0 mg |
| Corn starch | 40.0 mg | 38.9 mg |
| HPC (Klucel EF) | 3.0 mg | 3.0 mg |
| Calcium lactate · 5 H$_2$O | 100.0 mg | — |
| Lactic acid | 40.0 mg | — |
| Microcrystalline cellulose (Avicel PH 102) | 140.0 mg | 135.0 mg |
| Kollidon CL | 15.0 mg | 15.0 mg |
| Aerosil 200 | 9.0 mg | 9.0 mg |
| Magnesium stearate | 9.0 mg | 9.0 mg |

Using the components mentioned above, a tablet is prepared analogously to Example 4.

EXAMPLE 8

Three-layer tablet

|  | 1st layer | 3rd layer |
|---|---|---|
| Clotrimazole | 100.0 mg | — |
| Clindamycin-HCl (corresponds to 20 mg of clindamycin) | — | 22.7 mg |
| Lactose D20 | 265.0 mg | 265.0 mg |
| Corn starch | 33.0 mg | 33.6 mg |
| HPC (Klucel EF) | 2.0 mg | 2.0 mg |
| Calcium lactate · 5 H$_2$O | 90.0 mg | — |
| Lactic acid | 35.0 mg | — |
| Microcrystalline cellulose (Avicel PH 102) | 128.0 mg | 128.0 mg |
| Kollidon CL | 12.0 mg | 12.0 mg |
| Aerosil 200 | 7.0 mg | 7.7 mg |
| Magnesium stearate | 7.0 mg | 7.0 mg |

The second layer represents an intermediate layer which is located between the first and the third layers.

Intermediate layer:

| Lactose (Tablettose) | 58.7 mg |
|---|---|
| Avicel PH 102 | 30.0 mg |
| Aerosil | 0.5 mg |
| Magnesium stearate | 0.8 mg |
| Corn starch | 10.0 mg |

EXAMPLE 9

Two-layer tablet

|  | 1st layer | 2nd layer |
|---|---|---|
| Clotrimazole | 100.0 mg | — |
| Clindamycin-HCl (corresponds to 20 mg of clindamycin) | — | 22.7 mg |
| Lactose D20 | 265.0 mg | 93.7 mg |
| Corn starch | 33.0 mg | 20.0 mg |
| HPC (Klucel EF) | 2.0 mg | — |
| Calcium lactate · 5 H$_2$O | 90.0 mg | — |
| Lactic acid | 35.0 mg | — |
| Microcrystalline cellulose (Avicel PH 102) | 128.0 mg | 60.0 mg |
| Kollidon CL | 12.0 mg | — |
| Aerosil 200 | 7.0 mg | 1.6 mg |
| Magnesium stearate | 7.0 mg | 2.0 mg |

Using the components mentioned above, the first layer is granulated analogously to Example 1. The clindamycin-containing layer is not granulated but directly tableted with the granules of the first layer to give a two-layer tablet.

EXAMPLE 10

Tablet with effervescent composition (monolayer):

| Clotrimazole | 100.0 mg |
|---|---|
| Clindamycin-HCl (corresponds to 20 mg of clindamycin) | 22.7 mg |
| Lactose D20 | 265.0 mg |
| Corn starch | 33.3 mg |
| HPC (Klucel EF) | 2.0 mg |
| Calcium lactate · 5 H$_2$O | 90.0 mg |
| Lactic acid | 35.0 mg |
| Microcrystalline cellulose (Avicel PH 102) | 120.0 mg |
| Citric acid | 50.0 mg |
| Adipic acid | 10.0 mg |
| Aerosil 200 | 7.0 mg |
| Magnesium stearate | 7.0 mg |
| Sodium bicarbonate | 30.0 mg |

Clotrimazole, clindamycin-HCl, lactose, corn starch, HPC, calcium lactate and lactic acid are granulated in a fluidized-bed granulator.

The resulting granules are mixed with the other effervescent components and/or disintegrants and with microcrystalline cellulose, magnesium stearate and Aerosil, and tableted.

EXAMPLE 11

Vaginal cream:

One application unit is equivalent to 5 grams. This comprises 100 mg of clotrimazole and 20 mg of clindamycin.

One gram of cream has the following composition:

| | |
|---|---|
| Clotrimazole | 20.0 mg |
| Clindamycin-HCl (corresponds to 4 mg of clindamycin) | 4.54 mg |
| Sorbitan monostearate | 20.0 mg |
| Polysorbate 60 (Tween 60) | 15.0 mg |
| Cetyl palmitate (Cutina CP-A) | 30.0 mg |
| Viscous paraffin | 130.46 mg |
| Cetylstearyl alcohol | 100.0 mg |
| Benzyl alcohol | 10.0 mg |
| Purified water | 670.0 mg |

EXAMPLE 12

Ovulum (100/20):
Per ovulum, the following components are combined:

| | |
|---|---|
| Clotrimazole | 100.0 mg |
| Clindamycin-HCl (corresponds to 20 mg of clindamycin) | 22.7 mg |
| Calcium lactate · 5 H$_2$O | 77.3 mg |
| Gelatin | 250.0 mg |
| Purified water | 250.0 mg |
| Glycerol | 1250.0 mg |

EXAMPLE 13

Ovulum (100/20):
Per ovulum, the following components are combined:

| | |
|---|---|
| Clotrimazole | 100.0 mg |
| Clindamycin-HCl (corresponds to 20 mg of clindamycin) | 22.7 mg |
| Calcium lactate · 5 H$_2$O | 77.3 mg |
| Macrogol 400 | 1000.0 mg |
| Macrogol 6000 | 800.0 mg |
| Lactic acid | 200.0 mg |

EXAMPLE 14

Ovulum/suppository
Per ovulum, the following components are combined:

| | |
|---|---|
| Clotrimazole | 100.0 mg |
| Clindamycin-HCl (corresponds to 20 mg of clindamycin) | 22.7 mg |
| Calcium lactate · 5 H$_2$O | 77.3 mg |
| Hydrogenated fat | 1800.0 mg |

EXAMPLE 15

Ovulum (100/20):
Per ovulum, the following components are combined:

| | |
|---|---|
| Clotrimazole | 100.0 mg |
| Clindamycin-HCl (corresponds to 20 mg of clindamycin) | 22.7 mg |
| Calcium lactate · 5 H$_2$O | 77.3 mg |
| Hydrogenated fat | 1780.0 mg |
| Cetomacrogol 1000 | 20.0 mg |

EXAMPLE 16

The pharmaceutical composition according to the invention was used in a study involving 25 female patients. Among these 25 female patients, there were diagnosed 20 cases of bacterial mixed infections, 3 cases of mixed infections caused by bacteria and fungi and 2 cases of pure fungal infections.

After a 6-day-therapy with freshly prepared vaginal ovula comprising 20 mg of clindamycin and 100 mg of clotrimazole, the infection was completely cured in 23 of the female patients. Furthermore, secondary infections were not observed.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

What is claimed is:

1. A pharmaceutical composition, comprising:
   10 to 20 mg of clindamycin and from 50 to 100 mg of clotrimazole per application unit; and at least one pharmaceutically acceptable carrier.

2. The pharmaceutical composition of claim 1, wherein the formulation is adapted to vaginal administration.

3. The pharmaceutical composition of claim 1, wherein per application unit, the clindamycin is present in an amount of 20 mg and clotrimazole is present in an amount of 100 mg.

4. The pharmaceutical composition of claim 1 in the form of a monolayer tablet, effervescent tablet, two-layer tablet, three layer tablet, vaginal ring, suppository or ovulum for vaginal application.

5. The pharmaceutical composition of claim 3 in the form of a monolayer tablet, effervescent tablet, two-layer tablet, three layer tablet, vaginal ring, suppository or ovulum for vaginal application.

6. The pharmaceutical composition of claim 1 in the form of a semi-solid formulation.

7. A process for preparing a pharmaceutical composition of claim 1, wherein the active components clindamycin and clotrimazole are combined with at least one pharmaceutically acceptable carrier.

8. A method of treatment of a vaginal infection comprising: administering to a patient having a vaginal infection a pharmaceutical composition comprising 10 to 20 mg of clindamycin and 50 to 100 mg of clotrimazole and at least one pharmaceutically acceptable carrier.

9. The method of treatment of claim 8 wherein the pharmaceutical composition comprises 20 mg of clindamycin and 100 mg of clotrimazole per application unit.

10. The method of treatment of claim 8 wherein the pharmaceutical composition is in the form of a monolayer tablet, effervescent tablet, two-layer tablet, three-layer tablet, vaginal ring, suppository or ovulum for vaginal application.

11. The method of treatment of claim 9 wherein the pharmaceutical composition is in the form of a monolayer tablet, effervescent tablet, two-layer tablet, three-layer tablet, vaginal ring, suppository or ovulum for vaginal application.

12. The method of treatment of claim 8 wherein the pharmaceutical composition is a semi-solid formulation.

* * * * *